United States Patent [19]

Kam et al.

[11] Patent Number: 5,135,498
[45] Date of Patent: Aug. 4, 1992

[54] CONTROLLED RELEASE INFUSION DEVICE

[76] Inventors: Robert J. Kam, 324 N. 19th St., San Jose, Calif. 95112; Rolf A. Faste, 90 Peter Coutts Circle, Stanford, Calif. 94305; Anthony J. Castro, 2035 9th Ave., San Francisco, Calif. 94116

[21] Appl. No.: 503,720

[22] Filed: Apr. 2, 1990

[51] Int. Cl.$^5$ .......................................... A61M 37/00
[52] U.S. Cl. .................... 604/140; 604/131; 128/DIG. 12
[58] Field of Search ............... 604/140, 141, 131, 132, 604/133, 151, 143, 145, 146, 147; 128/DIG. 12

[56] References Cited

U.S. PATENT DOCUMENTS

| | | |
|---|---|---|
| 3,760,805 | 9/1973 | Higuchi . |
| 4,034,756 | 7/1977 | Higuchi et al. . |
| 4,191,181 | 3/1980 | Franetzki et al. . |
| 4,193,398 | 3/1980 | Refson . |
| 4,201,207 | 5/1980 | Buckles et al. . |
| 4,398,908 | 8/1983 | Siposs .................... 604/31 |
| 4,474,575 | 10/1984 | Eckenhoff et al. ........... 604/131 |
| 4,525,164 | 6/1985 | Loeb et al. ................. 604/131 |
| 4,552,561 | 11/1985 | Eckenhoff et al. ......... 604/131 X |
| 4,596,575 | 6/1986 | Rosenberg et al. .......... 604/891 |
| 4,898,582 | 2/1990 | Faste ........................ 604/141 |
| 4,969,874 | 11/1990 | Michel et al. .............. 604/140 |
| 4,969,884 | 11/1990 | Yum ....................... 604/141 X |

OTHER PUBLICATIONS

M. J. Sefton et al, "Controlled Release Micropump For Insulin Administration", Ann. Biomed. Eng., vol. 7, pp. 329–343, (1979).
J. Bottino et al., "Continuous Intravenous Arabinosyl Infusions Delivered by a New Portable Infusion System", Cancer, vol. 43, pp. 2197–2201, (1970).
S. Rose et al., "A Continuous Long-Term Injector", Austral. J. Biol., vol. 33, pp. 415–420, (1955).
Product Brochure, Pump Model AS-2F, -3B, -5B, -6C Copywrite Date 1979 Auto-Syringe, Inc. Hookset, New Hampshire.
Product Brochure, Pump Model ML6, Publication Date: 1981 Cormed, Inc., Middleport, N.Y.

Primary Examiner—John D. Yasko
Attorney, Agent, or Firm—Anthony J. Castro

[57] ABSTRACT

A means for elimination or compression of trapped air spaces in osmotically powered pumps is disclosed in which the housing of the pump is constructed of movable portions so that movement of the said housing portions will force air out of the device or compress it to such an extent that activation of the pump will result in the minimum lag time between activation of the pump and infusate flow.

19 Claims, 8 Drawing Sheets

CONTROLLED RELEASE INFUSION DEVICE

FIELD OF THE INVENTION

This invention relates to improved controlled release infusion devices, and particularly to small portable body-mounted devices capable of delivering liquids, such as drugs or other pharmaceutical agents for prolonged periods, where the liquid is contained in a flexible pouch within the device. The major effect of the improvement herein disclosed is to minimize dead air spaces that may exist in the device and effectively prime the pump to reduce delays between the time of initiation of the pump and the time of delivery of infusate.

BACKGROUND OF THE INVENTION

Many kinds of parenteral drug therapy require continuous drug delivery in preference to single or multiple drug injections. Benefits that accrue from continuous therapy may include, for instance, reduction of toxic or other side effects associated with sharp pulses of drug, significant improvement in the effectiveness of the therapy through the use of smaller amounts of drug, and increased patient comfort. The traditional manner of administering sustained parenteral treatments is via intravenous drip. Intravenous drip treatment is commonplace in a hospital environment, but this treatment mode obviously imposes severe restrictions on the activity of the recipient. As a result, considerable research over the last few years has been devoted to the development of small, portable infusion pumps. A range of devices has appeared, including those with electric or clockwork motors that drive syringe or peristaltic pumps, and others powered by the elastic tension of an inflated balloon, or the vapor pressure of a volatile propellant. Literature incorporated herein by reference describing such pumps are *Controlled Release Micropump for Insulin Administration*, (M. V. Sefton et al., Ann. Biomed. Eng., Vol. 7, pp. 329-343, 1979), *Continuous Intravenous Arabinosyl Cytosine Infusions Delivered by a New Portable Infusion System*, (J. Bottino et al., Cancer, Vol. 43, pp. 2197-2201, 1979), or product brochures from Auto-Syringe, Inc., Hooksett, N.H. and Cormed, Inc., Medina, N.Y. These devices are typically strapped onto the wearer, or carried on a belt or in a harness. Also, most are designed to deliver relatively large quantities of fluid and do not effectively dispense small volumes of the order of a few milliliters or less.

An alternative approach that has been exploited to a limited extent is to drive the infusion device osmotically, using a Rose-Nelson pump, activated by imbibition of water or other driving fluid. The principle of the osmotic pump was originally conceived by Rose and Nelson in the 1950's (S. Rose and J. F. Nelson, "A Continuous Long-Term Injector," *Austral. J. Exp. Biol.* 33, pp. 415-420 (1955)). A Rose-Nelson pump consists of three chambers: a salt chamber containing excess solid salt, a drug chamber, and a water chamber. The salt and water compartments are separated by a rigid membrane permeable to water but impermeable to ionized and hydrated salt ions; the salt and drug chambers are separated by a rubber diaphragm. In operation, water is imbibed osmotically into the salt chamber, causing the rubber diaphragm to expand into the drug chamber and forcing the drug out through the delivery orifice. Depending on the salt used, the osmotic pressure developed by this type of pump is usually between 50 and 200 atmospheres. The pressure required to pump the drug from the device is small in comparison, and hence the drug delivery rate remains constant as long as some excess undissolved salt remains in the salt chamber. In comparison with mechanically-driven devices, Rose-Nelson pumps are small, reliable, and simple and inexpensive to manufacture. U.S. Pat. No. 3,604,417 discloses a modification of the Rose-Nelson pump in which a movable piston replaces the elastic diaphragm separating the drug and salt chamber, and both the drug and salt are loaded into the pump as solutions. U.S. Pat. No. 4,474,048 discloses another modification of the Rose-Nelson principal employing an impermeable elastic wall, and a movable end wall that can be screwed in to deliver a pulse dose of the contained drug at any time during the operation of the pump. U.S. Pat. No. 4,474,575 is a variant of 4,474,048 in which the flow rate of the dispensed agent can be varied by altering the area of semipermeable membrane exposed to the water chamber. U.S. Pat. No. 4,552,651 discloses a pump assembly with a small osmotic pump that can be filled in advance of use with the active agent to be dispensed. The action of this pump is initiated by filling the lower chamber of the housing with a hydrogel. Once the pump is in action, an optional mechanism for delivering pulse doses can be employed. All these osmotic pumps are self-driven and begin to operate as soon as all of the several chambers are filled with their fluid contents and liquid is imbibed across the semipermeable membrane into the salt chamber.

U.S. Pat. No. 4,838,862, commonly owned with the present application and incorporated herein by reference in its entirety, describes a portable osmotic infusion pump that can be filled with the agent to be dispensed, the osmotic salt and the driving medium, and then stored as a complete assembly, ready for activation and use without need for addition of other components. U.S. Pat. No. 4,898,582, also commonly owned with the present application and incorporated herein by reference in its entirety, describes a portable osmotic pump that includes a housing with two side-by-side compartments, where one compartment contains the osmotic salt chamber, and the second compartment contains the imbibing liquid for the pump. The latter two patents describe osmotic pumps that can be filled with all required fluids, including the drugs to be delivered, stored until needed, and then activated very rapidly on demand. They are therefore excellent systems for use as disposable drug infusion devices.

Many limitations of these infusion devices, however, have not yet been addressed or resolved. Assembled infusion pumps contain trapped air spaces in a variety of areas such as the delivery lines, the needle assembly and interior spaces within the body of the device. Trapped dead air spaces impede the onset of infusate flow by attenuating the expansion effect of the motive force of the device. These dead space areas will accept the force developed by the motive power without a concomitant infusate flow. Infusate flow from the pump device will be delayed until all of the communicating air spaces are removed or compressed to the point where they do not affect infusate flow. Another common limitation of some of these systems is that the patient does not have control over activation of the device, or has, at best, only limited control. For example, if a device is activated by ingestion, it will begin to release drug as soon as it comes into contact with internal fluids. Another limitation is that, for many of these systems, the delivery rate of the infusate is not controlled, and, in particular, cannot be controlled by the user. A related problem is that, for many of these devices, the delivery rate of the infusate is controlled by directly regulating the flow of the infusate out of the device, for example, by a valve to control the flow rate. These configurations present problems with sterilization of the device, due to the presence of small compartments and crevices that will come in contact with the infusate that may be difficult for the sterilizing agent to reach. Another problem with flow regulation of the infusate fluid is that shear effects created, for example, by fluid passing through a valve, may lead to degradation of the molecules of drug in solution. For example, proteins or other large molecules are particularly susceptible to shear degradation. Moreover, reliable regulation of these very low flow rates is inherently difficult.

Yet another limitation of some of these devices is that long-term storage of the devices presents problems associated with drug stability and integrity. Many substances, such as drugs, fare poorly when stored, especially when stored in solution. The drug, when stored in a delivery device for a period of time may change or deteriorate chemically and pharmacologically, and may precipitate out of solution. The drug, under these conditions, may also react chemically with other components of the system that diffuse into the drug chamber from various parts of the assembly. This aspect of production, sterilization, and storage of a drug-bearing device is not adequately addressed in available disposable infusion devices and is a problem that therefore limits their use. Another limitation of some of these devices is related to the fact that there is, commonly, only one barrier between the infusate and driving medium, for example, a rubber diaphragm. This configuration creates potential safety problems for the user. Any tear or leak in the wall of the reservoir containing the infusate permits mixing of the infusate with the driving medium, which will result in contamination of the infusate. Such contamination would be potentially harmful to the patient if it happened during use, particularly if the driving fluid were contaminated by bacteria or other harmful substances. Clearly, it is possible to choose a driving medium that would not be harmful to the patient if this accidental mixing were to occur, but the requirement of sterilization of the driving medium, and preservation of the driving medium's sterility during use is yet another obstacle in the creation of a device that is simple and cost-effective to manufacture.

One means for resolving the problems of long-term infusate storage that is described in detail in this application is accomplished by containing the infusate in a removable flexible pouch within the device. In one embodiment of the invention, the pouch could be a part of the device that is filled with the infusate during manufacture, or later, for example by a pharmacist or other person, a short time before the device is used. There are many instances in the patent literature of infusion pumps where the liquid infusate is contained in a separate pouch within the device. U.S. Pat. No. 4,034,756 discloses a small osmotic pump for use in an aqueous environment, such as the gastrointestinal tract, in which the liquid infusate (e.g. a drug solution) is contained in a flexible bag within the device, and the osmotic fluid pressure is exerted directly on the flexible bag to effect infusate delivery. The flexible bag of this patent can be filled with the infusate during pump manufacture, or the bag can be filled with the infusate at a later time. This pump can be activated only by exposure to the aqueous environment, and is therefore limited generally to internal use for drug delivery. The activation means consists of the user swallowing the device or otherwise exposing the device to internal fluids, and rate control is soley a function of the permeability characteristics of the outer semipermeable layer.

U.S. Pat. No. 3,760,805 describes an osmotic dispenser comprised of a water porous housing confining a first flexible bag of relatively impervious material containing an active agent, and a second bag of controlled permeability to moisture containing an osmotic solution. The first and second bags are disposed within the housing such that water permeates from the external environment through the housing and migrates by osmosis into the solution contained in the second bag. The second bag increases in volume, thereby generating mechanical force on the first bag, which mechanical force in turn ejects the active agent out of the device. This pump, designed primarily for ingestion or implantation, depends upon permeation of water from the environment, e.g. gastrointestinal tract, and therefore is unsuitable for subcutaneous infusion.

U.S. Pat. No. 4,201,207 discloses an elastic bladder pump filled with liquid under pressure, which is powered by the elastic tension of the bladder. The bladder can be filled with infusate liquid during or after manufacture. This device also includes a flow control element between the bladder and the catheter fitting, to deliver the liquid infusate to the patient. Because the flow control element operates on the liquid infusate to be delivered, it has some of the attendant problems with shear effects and sterilization as described above. In addition, the bladder must be made of elastic materials, which are inherently permeable. The infusate is therefore vulnerable to absorption of contaminants by diffusion into the infusate from and through the bladder as well as loss of the drug by diffusion through the bladder if it is stored in the bladder for extended periods of time.

U.S. Pat. No. 4,191,181 discloses a liquid infusion pump with a power supply such as a battery and a refillable flexible infusate reservoir. This pump can be activated on demand and has a flow control means that acts directly on the pumping mechanism, which is downstream from the infusate reservoir. Therefore, the rate control means, in this case the pump mechanism, comes in direct contact with the infusate, causing the attendant problems with sterilization and shear effects described above.

U.S. Pat. No. 4,596,575 discloses an implantable liquid infusion pump that is particularly intended for the delivery of insulin. It contains two collapsible reservoirs in rigid housings, and also a mechanical pump that is regulated by an electronic unit control for management of pump activation and flow rate. One of the reservoirs contains the infusate; the space between the outer wall of this reservoir and its rigid housing is filled with the drive liquid. The second reservoir is filled with the drive liquid, and the space between the outer wall of this reservoir and its rigid housing is maintained at subambient pressure. The drive liquid is pumped from the second reservoir into the outer space of the first housing to exert pressure on the first reservoir and thus deliver the liquid infusate. The electronic control unit regulates two valves that restrict the flow rate of the drive liquid; thus the infusate does not come in contact with the valving system. The device is also provided with a separate refill system that may be used to refill the infusate reservoir. This type of refill mechanism, however, presents sterility problems during long-term use, particularly because it is used in an implantable device that cannot be cleaned during use. In addition, if the pouch wall breaks or tears, the infusate is susceptible to contamination from the driving medium, as described above.

Other patents in the literature describe portable infusion pumps that contain flexible pouches containing the infusate fluid that are removable from the device, or that can be loaded separately into the device after manufacture of the main pump assembly. U.S. Pat. No. 4,193,398, for example, discloses an extracorporeal osmotic pump in which the infusate liquid is contained in a flexible pouch that is located within a second pouch containing the osmotic fluid. In one embodiment, the infusate pouch can be removed from the main pump assembly and be replaced. This pump also contains an additional chamber filled with the driving medium for the pump, for example water or a weak osmotic solution, and incorporates rate-control and activation means. The osmotic fluid, however, has the potential to be in direct contact with the outer wall of the infusate pouch. Therefore, diffusion of the osmotic fluid into the infusate, and resulting damage, can occur if the infusate is stored within its pouch for any length of time in its fully assembled state. In addition, if the pouch wall breaks or tears, the infusate is susceptible to contamination from the osmotic fluid, as described above.

U.S. Pat. No. 4,398,908 discloses an infusion pump driven by electromechanical power, in which insulin is stored in a flexible pouch that is removable and replaceable, as is the pumping mechanism described. This pump can be activated on demand and incorporates a rate-control mechanism. The pumping mechanism, which incorporates the activation and rate-control means, is downstream from the insulin reservoir, and therefore comes in direct contact with the insulin infusate. As a result, this design has problems with sterilization of the pumping mechanism during manufacture, and shear effects on insulin during use, as described above. Insulin, being a large biomolecule in solution, is particularly susceptible to such damage.

U.S. Pat. No. 4,525,164 discloses a motor-driven pump with a removable and replaceable arcuated reservoir, in which a piston applies pressure directly to a portion of the reservoir to propel the drug out of the device. This device incorporates a means for activating the pump motor and controlling the pumping rate. Because the piston acts directly on the outer wall of the infusate reservoir, however, there is the possibility of shear effects on the infusate drug. Also, maintaining sterility in the pouch and pumping mechanism is difficult.

Each of these references describes an infusion pump that incorporates a separately loaded pouch or reservoir in a specific configuration, and usually with a specific motive force, yet all have problems that have inhibited their use. These problems include a high cost of manufacture, difficulties in sterilizing the drug chamber and contents, difficulties in maintaining sterility of the device, and problems with stability of the devices after prolonged storage. As a result, there remains a need for a reliable disposable infusion pump that can be loaded with sterile liquid infusate, that can maintain sterility during prolonged storage, and that can be activated on demand to provide the required pattern of delivery of very low infusate flow rates.

The present invention describes an infusion pump assembly that incorporates an infusate pouch that can be manufactured, sterilized, and aseptically loaded with infusate and assembled into a sterile pump assembly or sterilized separately from the other components of the assembly and then loaded into the pump assembly at the appropriate time. The pump is small, light, and convenient for patient use, and may be driven by a variety of motive forces in its different embodiments. The infusate pouch of this invention is simple in design, and therefore would be straightforward to manufacture and sterilize. It can also be made of nonelastic materials and therefore can be constructed using materials that are relatively impervious to invasion by environmental agents such as oxygen, carbon dioxide, or substances that are derived from components of the device. The rate of delivery of the infusate from this pouch is controlled by the expansion of a second pressure-transmitting pouch. Pressure is obtained by filling the second pressure-transmitting pouch with a driving medium at a controlled rate.

Presentation of sterile medication to the patient via infusion devices presents several unique problems in drug stability and sterility. Deposition of a drug solution into a cavity within an infusion device just prior to application requires presterilization of that cavity and delivery of a unit dose of sterile drug to the aforesaid cavity in an aseptic manner. Some methods of sterilization may be suited for some materials but totally unacceptable for other desired components. Many drugs and solutions may be rendered sterile by gamma radiation, but polypropylene components subjected to sterilizing doses of gamma radiation suffer severe radiation induced degradation. Metals may be advantageously sterilized using steam, but many drugs cannot withstand the steam sterilization regime. Separation filling and sterilization of the infusate pouch from the manufacture and treatment of the remainder of the infusion device permits optimization of the sterilizing procedure. For example, the infusate pouch may be manufactured and sterilized under conditions most suited for the materials of pouch construction. Then, at a later date, the sterile pouches may be aseptically filled with unit doses of drug solution that have been presterilized by conventional means; or alternately, the solutions may be sterilized by sterile filtration at the point of filling and the pouches sealed. These sterile dose units may then be assembled into the remainder of the infusion device or stored and shipped separately. Since the contents of the infusate pouch do not come into direct contact with the other components of the pump, it is not essential that the remainder of the device be manufactured and maintained under sterile conditions.

Drugs that have limited lifetimes in solution may be stored in a dry or lyophilized form in a two-compartment embodiment of the infusate pouch. In this pouch, one compartment contains the drug and another contains solvent for the drug in a separate sealed part of the pouch. The seal between the two compartments is broken just prior to use, the contents are mixed in the pouch, the pouch loaded into the infusion device, and the device is activated and attached. In this way, the shelf-life of the drug is dependent solely upon the storage conditions of the drug-containing infusate pouch.

SUMMARY OF THE INVENTION

Objects of the invention

It is an object of the invention to provide an improved portable controlled release infusion device that can be operated in such a manner so as to minimize the delay between activation of an infusion pump and the onset of infusate flow.

It is another object of the invention to provide a disposable portable controlled release infusion device that can be stored, with or without the infusate, for prolonged periods without deterioration.

It is another object of the invention to provide a portable controlled release infusion device wherein each individual device could potentially be used to deliver any of a variety of different liquids, including different drugs.

It is another object of the invention to provide a portable controlled release infusion device wherein the infusate is protected from contamination by other substances, particularly fluids, in the device, both during storage and use of the device.

It is another object of the invention to provide a portable controlled release infusion device that is inexpensive and straightforward to manufacture.

It is another object of the invention to provide a portable controlled release infusion device that can be easily sterilized and maintained in a sterile state.

It is another object of the invention to provide a portable controlled release infusion device that can be activated quickly and simply on demand.

It is another object of the invention to provide a portable controlled release infusion device wherein the flow rate of delivery of the liquid infusate can be controlled, either by the design of the device, or preferentially chosen by the user.

Other objects and advantages of the invention will be apparent to those of ordinary skill in the art from the description that follows.

DESCRIPTION OF THE INVENTION

Figure 1:
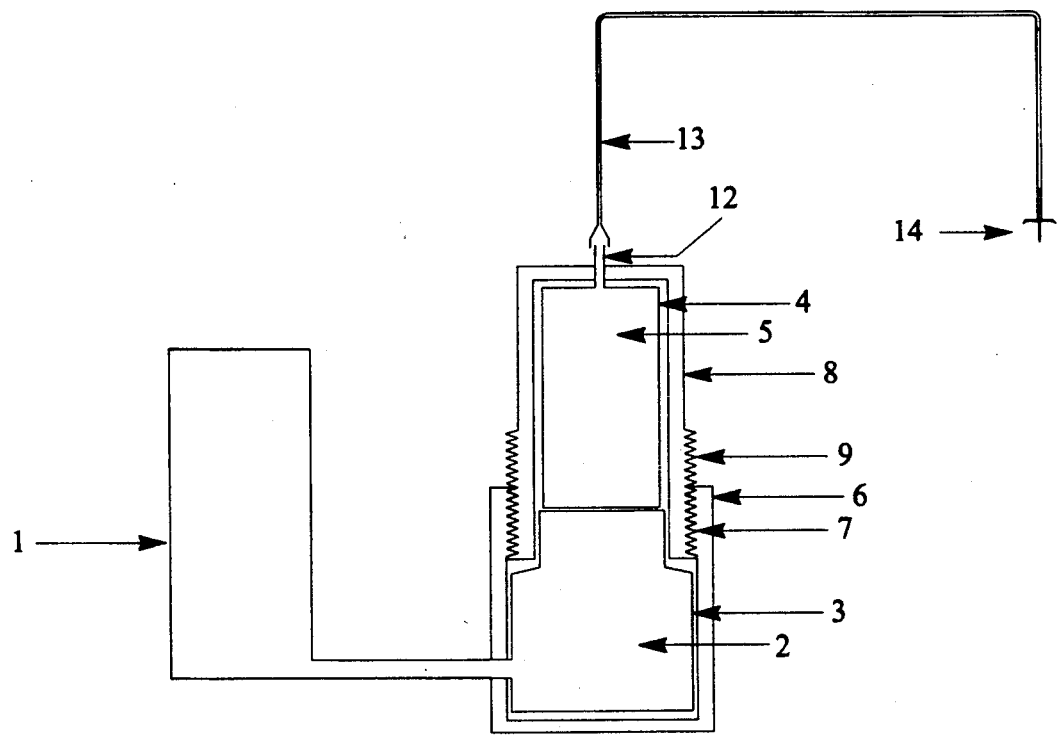
FIG. 1 is a diagram of the basic features of the invention wherein the infusion device is of cylindrical construction.

To achieve the foregoing objects, the present invention provides a portable controlled release infusion pump assembly. The assembly includes two chambers, where two containers (an elastic pouch and a flexible pouch) are held in the first chamber and a power source is contained in the second chamber. The first chamber is contained in a restraining outer housing that restricts movement of the two pouches. Preferably, the entire device is contained in a second unitary protective housing so as to protect the device from the environment. The protective housing can be made of metal or plastic, and would normally be made by any conventional mass-production technique. The dimensions of the housing will vary according to the volume of the chambers that are contained. The first chamber of the pump houses a first flexible pouch that is preferably sterilizable and under neutral pressure. This flexible pouch contains the infusate, preferably in liquid form. This first chamber also houses a second pouch, called the pressure-transmitting pouch, containing the driving medium as it is pumped in or created by the pressure-generating means. These pouches are positioned in the chamber with a minimal free volume between the pouches, and the pouches are in pressure transmitting relationship by which pressure is transmitted from the pressure-transmitting pouch to the pouch containing the infusate. Preferably, these two pouches completely fill the chamber in which they are placed. The assembly also includes a second chamber that contains the power source as herein defined, which consists of a pressure-generating means, an activating means, and a means of controlling the pressure increase or the rate of generation or transfer of the driving medium into the pressure-transmitting pouch, and thus the infusate flow rate out of the device. In a preferred embodiment, the pressure-generating means is based on the principle of osmosis as in the Rose-Nelson pump, described above. In other embodiments, the pressure-generating means is based on other motive principles, such as electrolysis, gas expansion, or elastic pressure and the like. In all cases, the pressure-generating means will cause the delivery of a medium, the driving medium, to the pressure-transmitting pouch, which will then exert pressure on the infusate delivery pouch. This driving medium can be a liquid or gas, and activation of the device by the user will cause delivery of the driving medium to the pressure-transmitting pouch. The rate at which the driving medium enters the pressure-transmitting pouch will be controlled by the rate-controlling means, which may be a membrane, in the case of a pump based on the Rose-Nelson principle, or in other embodiments of the device may be a valve for controlling fluid flow, or in still other embodiments of the device, may be a means of controlling current or voltage of an electric circuit. The resulting delivery rate of the infusate to the needle assembly is thus dependant on the pressure created in the pressure-transmitting pouch. The invention described herein is intended to deliver low flow rates, up to several milliliters per day, of infusate solution to the patient, and thus is primarily intended for subcutaneous, as opposed to intravenous, delivery. The infusion apparatus as herein described may be used for intravenous therapy where the flow rates of infusate are compatible with the intended intravenous therapy.

In the embodiment described above, the first chamber contains a pouch that contains the infusate. Because the infusate pouch can be manufactured and filled separately from the rest of the device, it can be sterilized in a manner optimal for the drug and the pouch material. Thus, drugs that are sensitive to radiation, steam, or ethylene oxide sterilization can be filled into presterilized pouches by sterilizing filtration under aseptic conditions. The remainder of the pump components may be sterilized under more rigorous conditions or not sterilized at all. In one embodiment, the infusate pouch and its contents are stored separately from the rest of the pump assembly under conditions particularly suited for the drug, thus greatly increasing the shelf life of the completely assembled pump. Because only the infusate pouch material, the needle assembly, and the delivery tube come in contact with the infusate solution, only these components need be sterile.

The infusate pouch is constructed of flexible material that is relatively impermeable to both the infusate contained (on its inner surface) and, as insurance against leakage of the pressure-transmitting pouch, the driving medium (on its outer surface), during storage and use. The material used for manufacture of this pouch should be flexible so that pressure applied by the pressure-transmitting pouch to the infusate pouch will cause delivery of the infusate. It is important that the materials used to fabricate the infusate pouch lack any substantial resistance to transmission of pressure developed in the pressure-transmitting pouch. That is, pressure developed in the pressure-transmitting pouch should be almost exactly transmitted to the infusate pouch, which will lead to flow of infusate out of the infusate pouch. Elastic materials can be used to form the infusion pouch, but are not preferred because most elastic materials are poor barriers to diffusion and could, in some cases, result in loss of the drug or permit interaction with chemicals diffusing into the infusate pouch from the driving medium, if this fluid should leak out of the pressure-transmitting pouch. In addition, elastic materials are typically more vulnerable to attack and degradation caused by infusate solutions. Therefore, preferred materials for the infusate pouch are polyethylenes, polypropylenes, Teflon ® (E.I. Du Pont de Nemours & Co., Wilmington, DE), Barex ® (BP Chemicals International, Cleveland, OH), Tedlar ® (Du Pont), and polyfoil laminates of materials such as polyethylene (facing the drug solution) and aluminum foil outside the pouch.

The infusate contained in the infusate pouch may be in its final fluid form ready for delivery. In some instances, however, it may be preferable to store the infusate, e.g. a drug, in a lyophilized or otherwise desiccated form, in order to prolong the storage time of the drug. This would be of particular interest if the infusate pouch were to be stored with the rest of the pump assembly during the entire shelf life of the device. Therefore, in an alternate embodiment, the infusate pouch will be segmented into two compartments. One compartment will contain a lyophilized form of the drug, and the other compartment will contain a pharmaceutically acceptable liquid solvent. In this embodiment, a seal between the two compartments would be broken by the user, or by a pharmacist or the like and the contents mixed before or during activation of the pump for use. To protect the infusate from degradation by diffusion of foreign substances into the drug-containing portion of the pouch during storage, and in particular the solvent, the seal must be made of impermeable materials. Preferred materials include metallized foil, metallized plastic film, and the like. This embodiment allows for storage of the infusate for long periods of time while insuring that the sterility of the pouch environment is not violated. In an alternate embodiment, the infusate pouch will contain a lyophilized form of the infusate, and the user or pharmacist will add a liquid solvent in an aseptic manner to the pouch either before or during activation of the pump.

As previously discussed, the pressure-transmitting pouch is in pressure transmitting relationship with the infusate delivery pouch and contains the driving medium as it is pumped into the pressure-transmitting pouch or generated by the power source. The pressure-transmitting pouch, and in particular the area that is in pressure transmitting relationship with the infusate delivery pouch, is made of flexible and preferably elastic materials so that it can exert pressure on the infusate pouch as driving medium fills the pressure-transmitting pouch. These materials of construction should have an extended life and should be impermeable to the driving medium received from the power source so that diffusion through the elastic walls will not contaminate the infusate during the lifetime of the device. Preferred elastic materials include conventional rubbers, ethylene-propylene, butadiene-styrene, neoprene, and the like. The pressure-transmitting pouch contains the driving medium as it is delivered by or created by the pressure-generating means. In the preferred embodiment of the Rose-Nelson osmotic pump, the driving medium is water. In this preferred embodiment, the pressure-transmitting pouch also contains the osmotic medium prior to activation of the device. Preferred osmotic mediums are salts, salt solutions, such as sodium chloride solution, and organic liquids such as polyethylene glycol. In other non-Rose-Nelson embodiments of the invention, preferred choices of driving medium are stable liquids such as glycerol, silicone oil, mineral oil, and the like, and gasses such as hydrogen gas. The use of an expanding pouch to transmit pressure to the infusate pouch has a number of advantages over the prior art. First, the driving medium is separated from the infusate by two impermeable films, i.e. the walls of the pressure-transmitting pouch and the walls of the infusate pouch. This means that even if one film should have a failure that would allow leakage of a confined material, the driving medium will not contaminate the infusate solution, although the pump may continue to deliver fluid out of the infusate pouch. Only in the very unlikely event of leaks or defects being found in both films would contamination occur. This is a considerable advantage over other designs in application for this type of device, where patient safety is a critical issue. A second problem avoided by this design is the need to make the housing for the infusate pouch and the pressure-transmitting pouch fluid-tight. It should be noted that devices that do not have a separate pressure-transmitting pouch containing the driving medium, for example the system described in U.S. Pat. No. 4,596,575, must be made absolutely leak-tight in order to function effectively. This type of construction is difficult to execute in an inexpensive, mass-produced unit, and leakage of the infusate or the driving medium in this type of device on prolonged storage is a serious problem. By containing the driving medium in a pouch, this problem is avoided. In the device described in this invention, it is desirable, however, to have relatively few air pockets in the spaces in the housing outside the pressure-transmitting pouch and the infusate pouch, or in the pressure-transmitting pouch itself. Although it is essential that the infusate pouch and the pressure-transmitting pouch are restrained in pressure transmitting relationship, which can most commonly be obtained by enclosing the pouches in a common housing, one of ordinary skill in the art can design alternative arrangements where the pouches are contained in separate housings and are attached in such a manner to achieve substantially the same results. The various components of this invention, power source, infusate pouch, pressure-transmitting pouch, activating means, rate-controlling means, may all be located within the same housing or in separate housing as convenience dictates, but are intended to be included within the scope of this invention provided that these components have the interrelationships as described herein.

The power source is the third major component of the pump assembly. As previously described, the power source consists of a pressure-generating means, an activation means, and a rate-controlling means. The pressure-generating means causes the delivery of the driving medium (gas or liquid) to the pressure-transmitting pouch. In the Rose-Nelson pump, the pressure-generating means would be the expansion of volume caused by permeation of a fluid through a semipermeable membrane into a salt chamber. Other pressure-generating means include, but are not limited to, electrolysis of a solution to produce a gas as a driving medium, expansion of a gas to generate pressure on a driving medium, storage of a fluid under pressure in an elastic compartment, and mechanical power sources, such as a spring or clock mechanism.

The activation means initiates the delivery of the driving medium to the pressure-transmitting pouch. Thus, the activation means allows for energizing of the pump at the user's discretion. For a Rose-Nelson pump design, the preferred activation means is rupturing of a seal that separates the permeant from the osmagent. Rupturing of the seal starts the osmotic process that makes it possible for the driving medium to enter the pressure-transmitting pouch. Another possible embodiment of the activation means is an on-off valve that allows the driving medium to enter the pressure-transmitting pouch. Another possible embodiment is a switch that closes an electrical circuit, or that activates a mechanical source of power.

The rate-controlling means controls the flow of driving medium into, or the creation of driving medium in, the pressure-transmitting pouch. It is a particular advantage of the present invention that the medium that is directly controlled is not the infusate, due to attendant problems with maintaining sterility of the rate-controlling means, and the need to avoid shear effects on the infusate. For a Rose-Nelson pump design, the rate-controlling means can be the semipermeable membrane. When the pump is in use, the permeant travels through the semipermeable membrane, and the rate of pumping of fluid to the pressure-transmitting pouch is thus controlled by the permeation properties of this membrane such as thickness, exposed area, permeation constant, etc. Because it is difficult to control the low flow rates with traditional valving (up to several milliliters per day), it is of particular advantage in this system that the rate-controlling means is inherent in the design. In another possible embodiment, rate-controlling means may be obtained by controlling an electrical resistance that varies the current or voltage in an electrical circuit. Another possible embodiment may make use of a mechanically controlled flow control valve.

The infusate leaves the infusate pouch through a dispensing nozzle and a connecting means. In one embodiment, the end of the connecting means may be adapted for use with a skin-piercing needle or a standard commercial subcutaneous drug delivery set, for example, the Sub-Q-Set® (Travenol Laboratories, Deerfield, IL). Alternately the tube may be inserted into one of the normal body orifices.

Activation of most pumps do not lead to instantaneous delivery of infusate. Delay time between activation of pumps and the appearance of infusate at the end of the delivery means is caused by the need to displace entrapped air from the delivery lines and expansion chambers and, in the case of osmotic pumps, the time lag observed before permeant penetrates the semipermeable membrane separating the permeant from the osmagent. In the instant invention, the delay in onset of delivery is eliminated or substantially reduced by constructing the pump so that first portion of the housing containing the infusate pouch is in slidable contact with the second portion of the housing, containing the pressure transmitting pouch or chamber, and providing a means for initiating contact between the first and second portions of the pump. By forcing the portions of the pump into contact, the entrapped air is expelled or compressed to the point where further compression of the air spaces will not take place without expulsion of infusate from the delivery means. In one embodiment of this invention, a cylindrical construction is employed wherein the first and second portions of the pump housing are connected with screw threads so that turning of the first portion with respect to the second portion by means of the screw threads compresses the two pouches into contact. Application of force is continued until liquid is expressed out of the delivery means. Activation of the device so as to increase pressure of the driving medium will cause that pressure to be transmitted to the infusate pouch and results in flow of infusate. In another embodiment, where the pump is non-cylindrical, the first and second portions of the pump are forced into contact by means of external clamps or latches or the like. Application of force is continued until liquid is expressed out of the delivery means. Activation of the device so as to increase pressure of the driving medium will cause that pressure to be transmitted to the infusate pouch resulting in flow of infusate. Excess entrapped air may be removed at the manufacturing site or, preferably shortly before or after activation of the pump.

The device assembly can be attached to the body of the wearer by means of a biocompatible adhesive coating on the base of the assembly, or by adhesive strips or overlays, and does not mandate the use of straps, belts, or other carrying garments. The device may be attached anywhere on the body that is convenient, either immediately adjacent to the delivery site, or at a point distant from that site.

Particularly when describing the power source of this invention, the various possible embodiments will employ components that are dependant on the motive force of the pump, driving medium used, the infusate being delivered, and other variables. The choice of components used in the various foregoing general descriptions and the following detailed descriptions are exemplary and explanatory, but are not restrictive of the invention.

Because the devices described in the present invention are small and simple, they are particularly suitable for delivering small infusate volumes. The pump assembly of this invention, while it can be tailored for a range of infusate volumes and dosage rates, is particularly useful where the total infusate volume to be dispensed is of the order of a few milliliters, and the delivery time for that volume is one to seven days. Thus, the invention enables therapy involving highly potent substances, such as peptide drugs of various kinds, heparin and insulin, analgesics and anesthetics, corticosteroids, immunosuppressants, antineoplastics, antibacterials, and antidotes to chemical or biological poisons and the like, to be administered without subjecting the patient to repeated injections or requiring the patient to be attached to an intravenous drip.

The infusion device can be assembled with all its components and stored for periods of months or years without deterioration. In a particularly preferred embodiment, the infusate is stored in the infusate pouch separately from the rest of the pump assembly. When ready for use, the patient or pharmacist or the like can insert the infusate pouch into the device. Eliminate the dead space to prime the pump and the device can then be activated on demand by the user or therapist.

DETAILED DESCRIPTION OF THE INVENTION

Definition of terms

The term "drug" as used herein denotes any medication composition (as defined, below); in any way affecting any human or animal entity; substance to be assimilated by any human being or animal for its nourishment or for regulating its growth; substance exhibiting any of the above activities to be directly applied to the habitat, surroundings or environment of any of the above organisms; and substance having any other effect on any other environment, especially any aqueous environment.

Therefore, suitable drugs for use with the dispenser of this invention include, without limitation, those that are generally capable of:

1. Preventing, alleviating, treating, or curing abnormal or pathological conditions of the living body by such means as destroying a parasitic organism or limiting the effect of the disease or abnormality by chemically altering the physiology of the host or parasite;

2. Maintaining, increasing, decreasing, limiting or destroying a physiologic body function, e.g. vitamin compositions, sex sterilants, fertility inhibitors, fertility promoters, growth promoters, and the like;

3. Diagnosing a physiological condition or state;

4. Controlling or protecting an environment or living body by attracting, disabling, inhibiting, killing, modifying, repelling, or retarding an animal or microorganism, such as food and nonfood baits, attractants and lures, biocides, pesticides, algicides, parasiticides, rodenticides, insecticides, fungicides, and the like;

5. Preserving, disinfecting, or sterilizing; and

6. Controlling or affecting generically an environment, as by introducing a catalyst or metering a reactant into a reacting chemical system, or by effecting any chemical process therein, such as fermentation, including propagation and/or attenuation of a microorganism.

Infusate is herein defined as a liquid drug or a solution, gel or suspension of drug that is delivered from the infusate pouch. Driving medium is herein defined as the material contained in the pressure-transmitting pouch that is used to increase the size of the pressure-transmitting pouch. If a gas is generated by the pressure generating means, the driving medium will consist, predominately of a gas. If pressure is generated osmotically, the driving medium will consist of the solution that results when the permeate passes through the semipermeable membrane and contacts the salt or salt solution (osmagent).

DETAILED DESCRIPTION OF THE FIGURES

Referring now to the drawings which are provided for illustration and not drawn to scale, a general plan of the invention is shown in FIG. 1. The power source 1, includes a pressure-generating means an activation means and a rate-controlling means. The pressure-generating means in this general plan can be chosen from a variety of motive sources, such as an osmotic pump of the Rose-Nelson type, electrolysis of a liquid to produce a gas as the driving medium, and others as described but not limited to the examples in the figures below. The pressure-generating means causes delivery of the driving medium 2 to the pressure-transmitting pouch 3. As driving medium enters the pressure-transmitting pouch, the pouch expands; therefore, the pressure-generating pouch must be made of a flexible or elastic material, and in particular the surface of the pressure-transmitting pouch facing and contacting the infusate pouch 4, which contains the infusate 5. Elastic materials are especially preferred because the surface of the pressure-transmitting pouch 3 that in pressure transmitting relationship with the infusate pouch functions best when it is expandable. Preferred elastic materials include conventional rubbers, ethylene-propylene, butadiene-styrene, neoprene, and the like. The pressure-transmitting pouch 3 may be made of a single material or can be made by gluing or heat sealing two or more dissimilar materials together to form the pouch.

The infusate pouch 4 is made of flexible materials, but normally is not made of elastic materials because most elastic materials are vulnerable to diffusion of the infusate out of the infusate pouch, or of diffusion of the driving medium into the infusate pouch, if that fluid should leak out of the pressure-transmitting pouch 3. In addition, elastic materials would typically be more vulnerable to attack and degradation caused by the infusate solution. Therefore, preferred materials for the infusate pouch 4 are inert polymers such as polyethylenes, polypropylenes, Teflon ® (E.I. Du Pont de Nemours & Co., Wilmington, DE), Barex ® (BP Chemicals International, Cleveland, OH), Tedlar ® (Du Pont), and polyfoil laminates of materials such as polyethylene (facing the infusate solution) and aluminum foil comprising the outer surface the infusate pouch. It is a major advantage of this invention that the infusate solution contacts inert, stable, sterilizable, nonleaching materials, and is essentially impervious to contaminants from the outside environment. In one embodiment, the infusate pouch 4 is formed and filled with infusate solution in a single operation using a heat-sealing form-fill-and-seal technology widely used industry today. This technology is used, for example, to form small polyfoil bags containing foods such as ketchup and mustard or transdermal drug delivery systems. This technology is amenable to very high production rates at low cost and can be maintained under aseptic conditions.

The pressure-transmitting pouch 3 is contained in housing 6 and infusate pouch 4 is contained in a housing 8, both of which are in restraining relationship to both pouches and should be made of a substances that nonirritating to the skin and nonreactive and impervious to the salts, solutions, agents and the like, contained therein. Housing 6 is connected to housing 8 by means of screw threads 7 and 9 respectively. In one embodiment, this housing also encloses the power source, so as to protect it from the environment. Preferred materials for housings 6 and 8 are stainless steel, aluminum, polyolefins, polycarbonate and the like. An infusate connecting means 13 is attached to the dispensing nozzle 12 of the infusate pouch by means and by means of the needle assembly 14, to the patient. The needle assembly may be a skin-piercing needle or a standard commercial subcutaneous delivery set, for example, the Sub-Q-Set ® (Travenol Laboratories, Deerfield, IL.). Alternately the infusate delivery tube may be inserted into one of the normal body orifices. A pump of this type is primed by turning the two halves of the housing until liquid is expressed out the delivery nozzle or the needle set.

Figure 2:
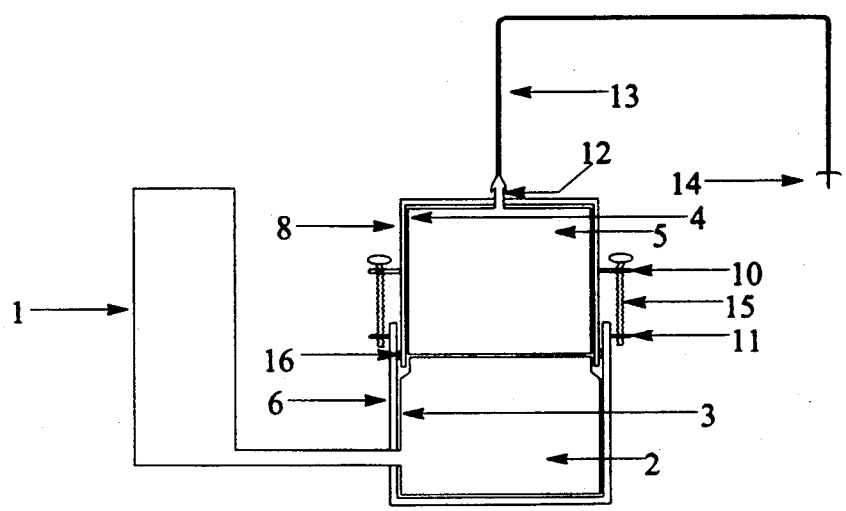
FIG. 2 is a diagram of the basic features of the invention wherein the infusion device is of non-cylindrical construction.

Referring again to the drawings, a general plan of the invention is shown in FIG. 2. The power source 1, includes a pressure-generating means, an activation means and a rate-controlling means. The pressure-generating means in this general plan can be chosen from a variety of motive sources, such as the osmotic pump of the Rose-Nelson type, electrolysis of a liquid to produce a gas as a driving medium, and others as described but not limited to the examples in the figures below. The pressure-generating means causes delivery of the driving medium 2 to the pressure-transmitting pouch 3. The pressure-transmitting pouch 3 is contained in housing 6 and infusate pouch 4 is contained in a housing 8, both of which are in restraining relationship to both pouches and should be made of a substances that nonirritating to the skin and nonreactive and impervious to the salts, solutions, agents and the like, contained therein. Housing 6 is connected to housing 8 by means of screw threads 15 attached to screw supports 10 and 11 placed on housings 6 and 8 respectively, so that application of force on the screw will compress the first and second portions 6 and 8. An O-ring 16 is provided to facilitate the movement of the two halves of the housing. In one embodiment, this housing also encloses the power source, so as to protect it from the environment. Preferred materials for housings 6 and 8 are stainless steel, aluminum, polyolefins, polycarbonate and the like. An infusate connecting means 13 is attached to the dispensing nozzle 12 of the infusate pouch by means and by means of the needle assembly 14, to the patient. The needle assembly may be a skin-piercing needle or a standard commercial subcutaneous delivery set, for example, the Sub-Q-Set ® (Travenol Laboratories, Deerfield, IL.). Alternately the infusate delivery tube may be inserted into one of the normal body orifices.

Figure 3:
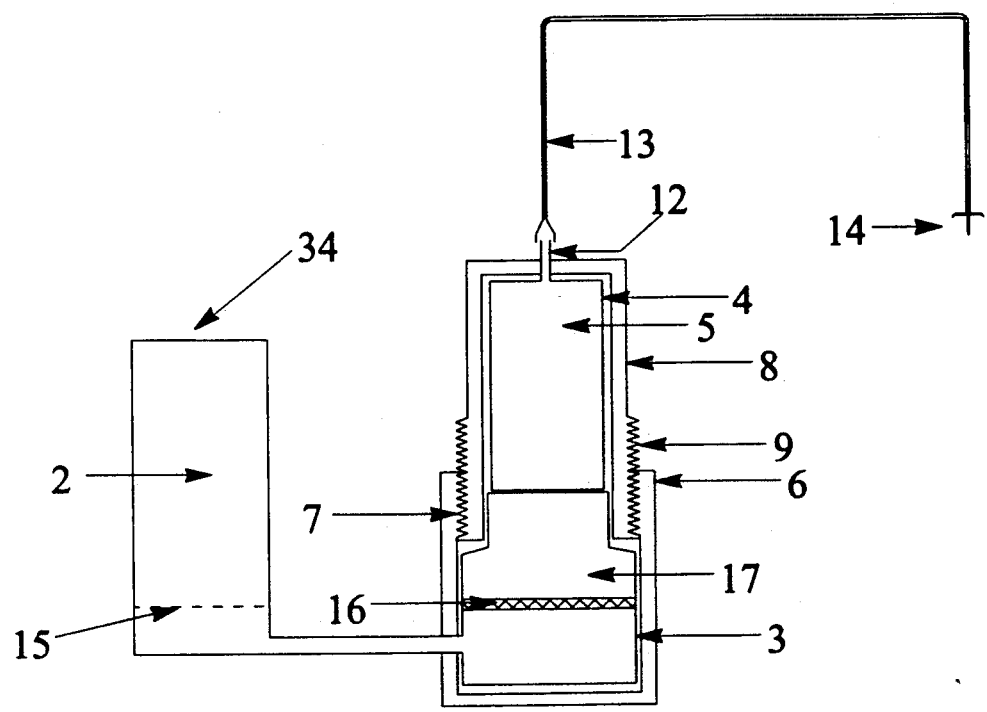
FIG. 3 is a diagram of an embodiment of the invention for which the motive force is the osmotic principle as in the Rose-Nelson pump.

FIGS. 3, 4, 5, 6, 7 and 8 are illustrations of embodiments of the general plan illustrated in FIG. 1 and FIG. 2. FIG. 3 illustrates a device based on the principle of the Rose-Nelson osmotic pump. The permeant 2 for this pump is normally water, although any liquid capable of generating an osmotic pressure in conjunction with the osmagent could be used. Before activation of the device, the permeant 2 is contained in chamber 34 separated from contact with the semipermeable membrane 16 and the pressure-transmitting pouch 3 by a seal 15 that is ruptured immediately prior to use by the patient. The semipermeable membrane 16 is shown in FIG. 3 as being contained within the first chamber, but it can alternately be contained in chamber 34. The seal 15 is made from metal foil, metallized film or the like. When the device is in use, the permeant travels through the semipermeable membrane 16 into the osmotic pouch 3 which contains an osmagent that may be a salt tablet or osmotic solution. The delivery rate of the pump depends on the area, thickness, and permeability of the semipermeable membrane. Hence the choice of a suitable membrane material is essential to good performance of the pump. A preferred choice is a membrane made from one of the cellulose esters or ethers, such as cellulose acetate or cellulose butyrate. It is a particular advantage of this system that the rate-controlling means is inherent in the design, because with traditional valving it is difficult to control the low flow rates (up to several milliliters per day) in question. A wide range of appropriate solutes and membrane materials for use in osmotic pumps is disclosed in U.S. Pat. No. 4,034,756, which is incorporated herein by reference. Preferred salts are sodium chloride, potassium chloride, magnesium sulfate, and sodium sulfate. The osmotic pressure developed by the diffusion of the permeant 2 into the osmotic pouch 3 creates pressure that is exerted on the infusate pouch 4 by the driving medium 17, and the infusate is delivered as described in FIG. 1 above. Osmosis is in general a rather slow constant process, and thus in general this type of device is preferred when infusion of a rather small volume of infusate in the range of 0.01 to 5 mL per day, at a constant rate over 12 hours to 7 days, is required. A pump of this type is primed by turning the two halves of the housing until liquid is expressed out the delivery nozzle or the needle set.

Figure 4:
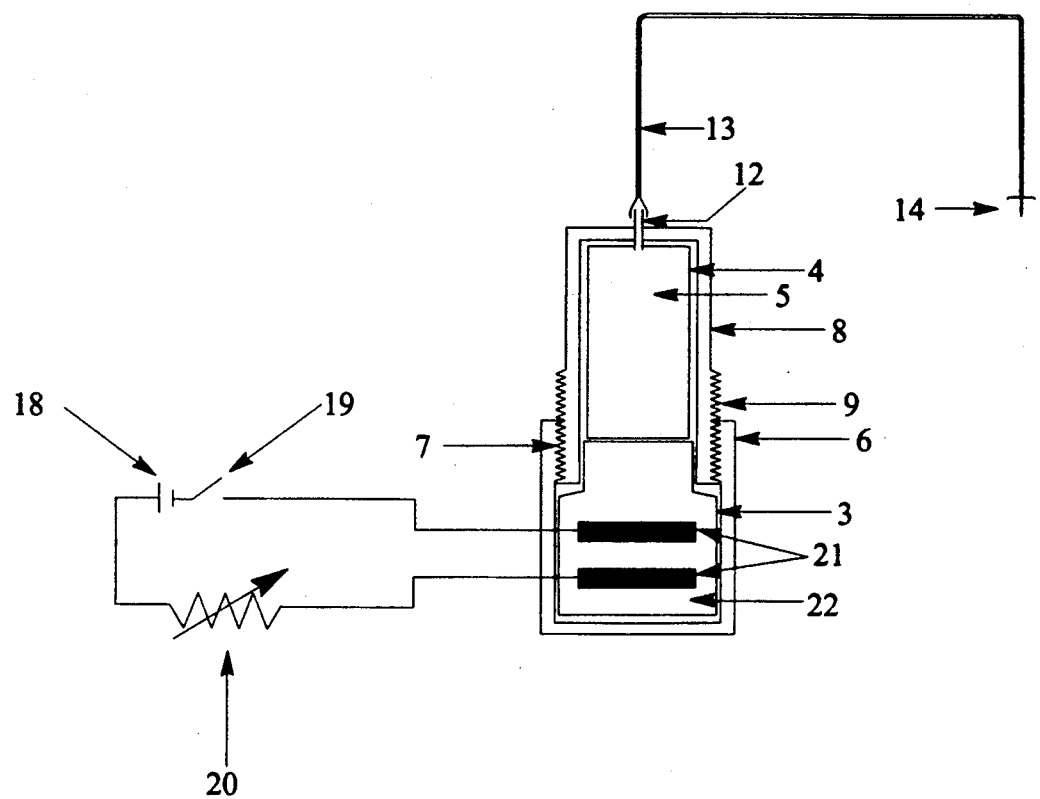
FIG. 4 is a diagram of an embodiment of the invention for which the motive force is electrolysis of a fluid to produce a gas that will act as the driving medium.

FIG. 4 is an illustration of another embodiment of the invention in which the motive force for the pump is provided by electrolysis of a solution to produce gas as a driving medium. The device is activated by a switch 19, that completes an electric circuit consisting of a battery or other power source 18, and a resistance 20. Rate control of the device is achieved either by variation of the voltage or current at the power source 18. A set of electrodes 21, is connected to the electric circuit and is contained in the pressure-transmitting pouch, 3. Preferred materials for these electrodes include nickel, palladium, platinum, or other inert materials. The application of current to the electrodes 21, which are immersed in a solution 22, such as sodium sulfate, causes the formation of gas bubbles, for example, bubbles of hydrogen gas. Pressure caused by formation of the gas bubbles is exerted on the area in pressure transmitting relationship between the pressure-transmitting pouch 3 and the infusate pouch 4, and infusate 5 is delivered to the patient as described in FIG. 1. Because large volumes of gasses can be quickly generated by small currents, this type of device is preferred when relatively rapid delivery of the infusate solution is required over a period of a few hours to one day. A second advantage of this unit is that the rate of gas generation, and hence infusate delivery, can be easily changed by varying the voltage or current in the electric circuit. This device therefore allows pulses of infusate to be delivered to the user on demand. This type of system would find an application, for example, in insulin therapy for treatment of diabetes, or analgesic therapy for pain relief. A pump of this type is primed by turning the two halves of the housing until liquid is expressed out the delivery nozzle or the needle set.

Figure 5:
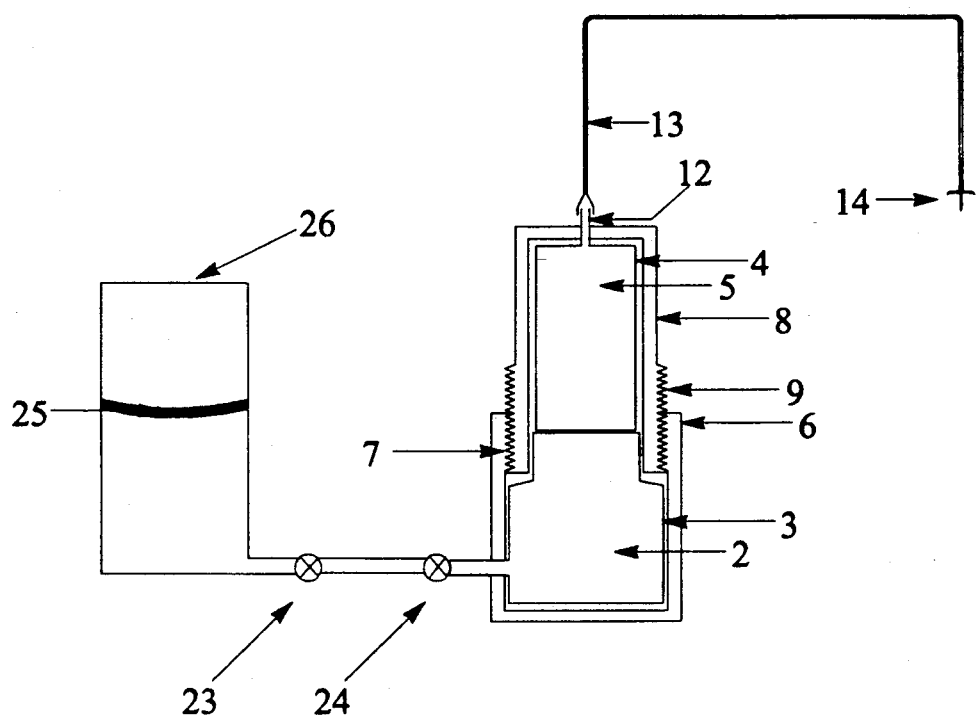
FIG. 5 is a diagram of an embodiment of the invention for which the motive force is an expanding gas that exerts pressure on the driving medium.

FIG. 5 is an illustration of another embodiment of the invention in which the motive force for the pump is provided by the expansion of a gas under pressure. The gas under pressure is stored in a compartment of the pressure-generating compartment 26 that is separated from the adjoining compartment by an elastic diaphragm 25. This elastic diaphragm must be impermeable so as it prevent migration of the gas into the driving medium during storage, or migration of the driving medium into the gas. Therefore, preferred materials for the impermeable elastic diaphragm include latex rubber, polyisoprene, butyl rubber, nitrile rubber, copolymers of styrene/butadiene, and the like. This gas may be stored as a liquid propellant that vaporizes upon contact with the body; a problem with such a motive means, however, is that the gas pressure will vary with the body temperature, and in particular that a low body temperature would be insufficient to cause sufficient vaporization of the propellant. Therefore, a propellant should be chosen that will vaporize below body temperature at 1 atm, for example, hydrochlorofluorocarbons, or fluorocarbons such as the Freon ® refrigerants (E.I. du Pont de Nemours & Co., Wilmington, DE); especially preferred are the Freon refrigerants such as Freon 114 and Freon 21, which vaporize at 3.77° C. and 8.92° C., respectively, at 1 atm. Pump action begins after activation means 23 is turned on; this activation means is typically an on-off valve such as a gate valve. When activation means 23 is turned on, the driving medium 2 in the second compartment of the pressure-generating compartment is allowed to flow into pressure-transmitting pouch 3. Preferred choices of driving medium 2 are stable liquids such as water, glycerol, silicone oil, mineral oil, and the like. The flow rate of the driving medium 2, and therefore the flow rate of infusate from the device, is controlled by manipulation of rate-controlling means 24, which is a valve suitable for controlling liquid flow rates in the range, for example, of 0.01 to 5 mL/day. One embodiment of rate-controlling means 24 is an elastomeric micrometering system, consisting of axially-aligned elastic fibers contained in an elastic tube, with a clamping means to adjust the cross-sectional free area in the tube available for fluid flow, as described in *An Elastomeric Micrometering System for the Controlled Administration of Drugs* (J. C. Wright et al., Rubber Chemistry and Technology, Vol. 50, No. 5, pp. 959–968, 1977). As the driving medium enters the pressure-transmitting pouch 3, this pouch exerts pressure on infusate pouch 4 through the area in pressure transmitting relationship between pouch 3 and pouch 4, and infusate is delivered to the patient as described in FIG. 1. A pump of this type is primed by turning the two halves of the housing until liquid is expressed out the delivery nozzle or the needle set.

Figure 6:
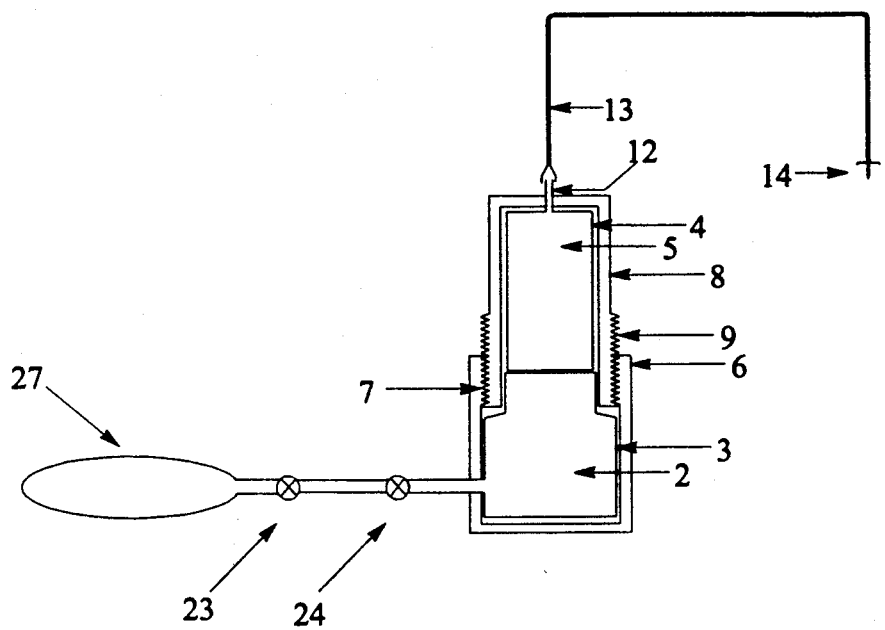
FIG. 6 is a diagram of an embodiment of the invention for which the motive force is the elastic tension of a driving medium under pressure in an elastic compartment.

FIG. 6 illustrates an embodiment of the invention in which the motive force is the elastic tension of a bladder containing a driving medium under pressure in an elastic compartment. The driving medium 2 is contained in elastic compartment 27 under pressure; preferred choices of driving medium 2 are as in FIG. 5. Preferred materials for the elastic compartment include conventional rubbers, ethylene-propylene, butadiene-styrene, neoprene, and the like. As in the embodiment of the invention described in FIG. 5, the device is turned on using activation means 23, and flow rate of the driving medium, and therefore the infusate, is controlled by rate-controlling means 24. The driving medium is delivered to pressure-transmitting pouch 3, and pressure on infusate pouch 4 results in delivery of the infusate to the patient, as described in FIG. 1. A pump of this type is primed by turning the two halves of the housing until liquid is expressed out the delivery nozzle or the needle set.

Figure 7:
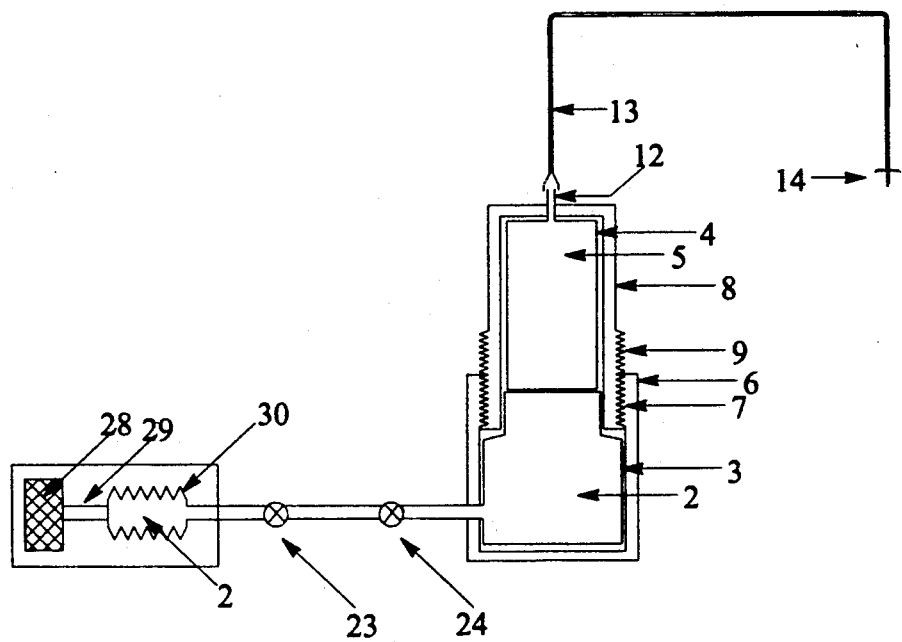
FIG. 7 is a diagram of an embodiment of the invention for which a mechanical or electromechanical motive force drives the device.

FIG. 7 illustrates an embodiment of the invention in which a mechanical motive force 28, drives the pump, i.e. a mechanical pressure generating means creates a force that acts on piston 29 which subsequently exerts pressure on driving medium compartment 30 and forces driving medium 2 out of the compartment. Preferred choices for driving medium 2 are stable liquids such as water, glycerol, silicone oil, mineral oil, and the like. A preferred choice for this mechanical motive power source is a battery-powered motor with so-called "Accutron" movement made by the Bulova Watch Company (Flushing, N.Y.). A movement of this kind is relatively light in weight and can be obtained in a design that will turn one revolution per day, so as to drive a drive wheel and piston at one revolution per day. At this speed output a piston can be made to produce approximately 0.42 ounce/inch of torque and with a very nominal increase in speed at this loading. In this system, the rate-controlling means 23 could simply be a means of controlling motor speed, since the rate of delivery of the driving medium is controlled by the motor speed. Another preferred choice for a mechanical pressure generating means is a mechanical spring assembly constructed with of a plurality of constant-force extendable coil springs. The extended ends of the spring coils are secured to the piston, which acts upon driving medium compartment 30 upon activation of the device. Thus the spring coils apply a low intensity, constant force to driving medium compartment 30 for developing a small positive pressure on the driving medium 2 contained within the compartment. The device is turned on with activation means 23, which in one embodiment is a solenoid switch, and the flow of driving medium is regulated with rate-controlling means 24, which in one embodiment is a controlled motor speed, as described above. In another embodiment, rate-controlling means 24 is a valve intended for regulating low flow rates as described in FIG. 5. The driving medium 2 is pumped into pressure-transmitting pouch 3, and the force applied to the infusate pouch 4 causes the infusate 5 to be delivered to the patient, as described in FIG. 1. This type of mechanical driving force is preferred for relatively constant delivery infusion systems. A pump of this type is primed by turning the two halves of the housing until liquid is expressed out the delivery nozzle or the needle set.

Figure 8:
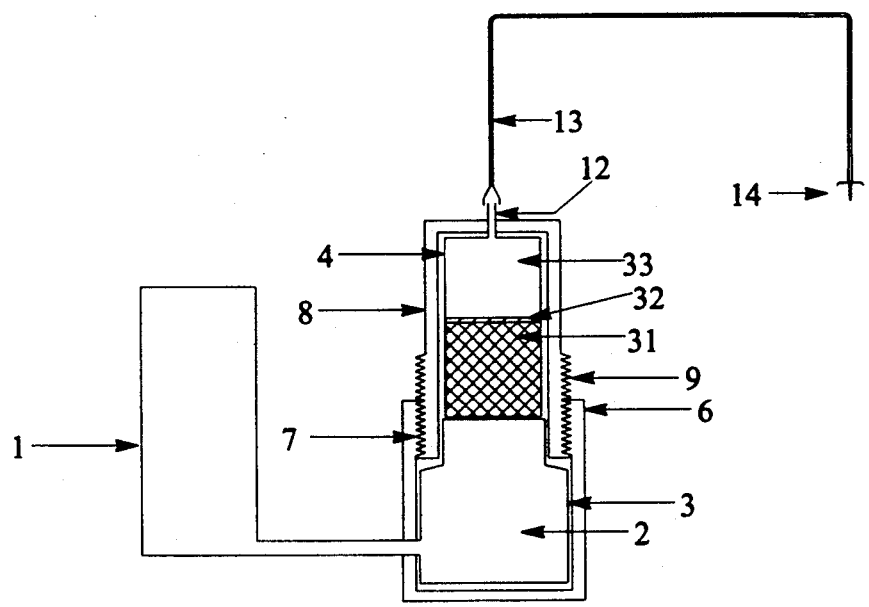
FIG. 8 is a diagram of an embodiment of the invention for which the infusate is contained in lyophilized form in a pouch with two compartments, with a breakable seal separating the infusate from a liquid solvent.

Another embodiment of the invention, shown in FIG. 8, infusate pouch 4 is divided into two compartments for the purpose of storing the drug 31 in lyophilized or otherwise desiccated form, so as to prolong the shelf life of the drug. In this embodiment, one compartment of infusate pouch 4 contains lyophilized drug and is separated from the solvent compartment of pouch 4 by rupturable seal 32. This seal 32 must be impermeable to both the lyophilized drug 31 and the liquid solvent 33, therefore, a preferred material for this seal is a metallized foil, metallized plastic film, or the like. Seal 32 is ruptured by the user immediately before or during activation of the device, to allow mixing of lyophilized drug 31 and liquid solvent 33 before delivery of the infusate to the patient. A pump of this type is primed by turning the two halves of the housing until liquid is expressed out the delivery nozzle or the needle set.

The invention has been described and illustrated with reference to certain preferred embodiment thereof but, those skilled in the art will appreciate that various modifications, changes, omissions, and substitutions can be made without departing from the spirit of the invention. For example, one skilled in the art might construct the infusion pouch with a fill port so that it may be filled by the user, pharmacist, or the like, just prior to activation. It is intended, therefore, that the invention be limited only by the scope of the following claims. One skilled in the art may also construct a pump containing the infusate in a compartment that is not pouch-like but of conventional design and utilize movable portions of the housing to effect elimination or compression of air spaces and effectively diminish the lag time between activation of the pump and the appearance of infusate flow and be within the scope and teaching of this invention. The invention herein described is intended to deliver low flow rates of infusate solution to the patient. For example, such a device might be sized to contain an infusate volume of from 1 to 20 milliliters, and to deliver this volume over a period of from two hours to seven days. The specific volume of infusate contained and total delivery time would vary depending on the choice of infusate, and would not necessarily be restricted to these quantities.

We claim:

1. A portable infusion device assembly comprising:
   a. a first pouch containing infusate and a dispensing nozzle,
   b. a second pouch containing a driving medium in pressure transmitting relationship to the aforesaid first pouch,
   c. an integral power source comprising:
      a pressure generating means for generating pressure in aforesaid driving medium,
      an activating means for initiating the action of the aforesaid generating means,
      a rate controlling means for regulating the volume change of the aforesaid first pouch,
   d. a connecting means for attaching the aforesaid dispensing nozzle to the object of treatment and,
   e. a first rigid housing in restraining relationship containing the aforesaid first pouch and in sliding relationship with a second housing
   f. a second rigid housing in restraining relationship containing the aforesaid second pouch and in sliding relationship with aforesaid first housing and,
   g. a means for initiating flow of infusate by forcibly moving aforesaid first and second housings in such a manner as to compel and maintain contact between aforesaid first and second pouches.

2. A portable infusion device assembly comprising:
   a. a first pouch containing infusate and a dispensing nozzle,
   b. a second pouch containing a driving medium in pressure transmitting relationship to the aforesaid first pouch,
   c. an integral power source comprising: a pressure generating means for generating pressure in aforesaid driving medium, an activating means for initiating the action of the aforesaid generating means, a rate controlling means for regulating the volume change of the aforesaid first pouch,
   d. a connecting means for attaching the aforesaid dispensing nozzle to the object of treatment and,
   e. a rigid housing containing the aforesaid first pouch, second pouch and power source and in restraining relationship with the aforesaid first and second pouches, and
   f. a means for initiating flow of infusate by forcibly moving aforesaid first and second housings in such a manner as to compel and maintain contact between aforesaid first and second pouches and power source.

3. The device according to claim 1 where:
   a. the pressure generating means is comprised of:
      an osmagent and,
      a liquid permeant and,
   b. the rate controlling means is comprised of a semipermeable membrane and,
   c. the driving fluid is produced when permeant contacts osmagent.

4. The device according to claim 1 where:
   a. the pressure generating means is comprised of:
      a gas generating electrolytic cell,
   b. the rate controlling means is a electrical circuit operated is such a manner as to control the rate of gas formation and,
   c. the operating medium is gaseous.

5. The device according to claim 1 where:
   a. the pressure generating means is comprised of:
      a gas under pressure,
   b. the rate controlling means is a valve operated is such a manner as to control the rate of gas flow and,
   c. the operating medium is gaseous.

6. The device according to claim 1 where:
   a. the pressure generating means is comprised of:
      a mechanical means for increasing the pressure of the pressure-transmitting pouch,
   b. the rate controlling means is obtained by operating the aforesaid mechanical means in such a manner so as to control the rate of pressure formation and,
   c. the operating medium is liquid.

7. The device according to claim 1 where:
   a. the pressure generating means is comprised of:
      a mechanical means for increasing the pressure of the pressure-transmitting pouch,
   b. the rate controlling means is obtained by operating the aforesaid mechanical means in such a manner so as to control the rate of pressure formation and,
   c. the operating medium is gaseous.

8. The device according to claim 2 where:
   a. the pressure generating means is comprised of:
      an osmagent and,
      a liquid permeant and,
   b. the rate controlling means is comprised of a semipermeable membrane and,
   c. the driving fluid is produced when permeant contacts osmagent.

9. The device according to claim 2 where:
   a. the pressure generating means is comprised of:
      a gas generating electrolytic cell,
   b. the rate controlling means is a electrical circuit operated is such a manner as to control the rate of gas formation and,
   c. the operating medium is gaseous.

10. The device according to claim 2 where:
    a. the pressure generating means is comprised of:
       a gas under pressure,
    b. the rate controlling means is a valve operated is such a manner as to control the rate of gas flow and,
    c. the operating medium is gaseous.

11. The device according to claim 2 where:
    a. the pressure generating means is comprised of:

a mechanical means for increasing the pressure of the pressure-transmitting pouch, b. the rate controlling means is obtained by operating the aforesaid mechanical means in such a manner so as to control the rate of pressure formation and, c. the operating medium is liquid.

12. The device according to claim 2 where:

a. the pressure generating means is comprised of:
a mechanical means for increasing the pressure of the pressure-transmitting pouch, b. the rate controlling means is obtained by operating the aforesaid mechanical means in such a manner so as to control the rate of pressure formation and, c. the operating medium is gaseous.

13. A method for infusing a patient, comprising connection of said patient to a portable infusion device, said device comprising:

a. a first pouch containing infusate and a dispensing nozzle, b. a second pouch containing a driving medium in pressure transmitting relationship to the aforesaid first pouch, c. an integral power source comprising:
a pressure generating means for generating pressure in aforesaid driving medium,
an activating means for initiating the action of the aforesaid generating means,
a rate controlling means for regulating the volume change of the aforesaid first pouch, d. a connecting means for attaching the aforesaid dispensing nozzle to the object of treatment, e. a rigid housing in restraining relationship containing the aforesaid first and second pouches and, f. activating said device.

14. A method for infusing a patient, comprising connection of said patient to a portable infusion device, said device comprising:

a. a first pouch containing infusate and a dispensing nozzle, b. a second pouch containing a driving medium in pressure transmitting relationship to the aforesaid first pouch, c. an integral power source comprising:
a pressure generating means for generating pressure in aforesaid driving medium,
an activating means for initiating the action of the aforesaid generating means,
a rate controlling means for regulating the volume change of the aforesaid first pouch, d. a connecting means for attaching the aforesaid dispensing nozzle to the object of treatment and, e. a rigid housing in restraining relationship containing the aforesaid first pouch, second pouch and power source and in restraining relationship with the aforesaid first and second pouches, f. a means for initiating flow of infusate by forcibly moving aforesaid first and second housings in such a manner as to compel and maintain contact between aforesaid first and second pouches and power source.

g. initiating infusate flow by forcibly moving aforesaid first and second housings and, h. activating said device.

15. A method for facilitating infusate flow from an infusion device comprising:

a. an infusate compartment, b. a dispensing nozzle for delivering infusate from said infusate compartment, c. a force means for generating and applying continuous pressure to said infusate compartment sufficient to cause infusate flow, d. a housing in restraining relationship to said infusate compartment and force means comprised of portions in moveable relationship in that movement of said portions will cause elimination or compression of trapped air spaces so that activation of the force means will produce infusate flow without significant delay.

16. A method according to claim 15 where trapped air space is eliminated or compressed before activation of the force means.

17. A method according to claim 15 where trapped air space is eliminated or compressed simultaneous with activation of the force means.

18. A method according to claim 15 where trapped air space is eliminated or compressed shortly after activation of the force means.

19. A portable infusion device assembly comprising:

a. dispensing nozzle.

b. infusate, c. a driving medium in pressure transmitting relationship to the aforesaid infusate, d. an integral power source comprising:
a pressure generating means for generating pressure in aforesaid driving medium,
an activating means for initiating the action of the aforesaid pressure generating means,
a rate controlling means for regulating the volume change of the aforesaid infusate, e. a connecting means for attaching the aforesaid dispensing nozzle to the object of treatment, f. a rigid housing in restraining relationship containing the aforesaid infusate and pressure generating means and, g. a means for displacing or compressing contained air spaces in the aforesaid rigid housing.

* * * * *